United States Patent [19]

Shibanai

[11] Patent Number: 4,617,147
[45] Date of Patent: Oct. 14, 1986

[54] PROCESS FOR PREPARATION OF SOLID PERFUMES

[76] Inventor: Ichiro Shibanai, 10-6-312, Akasaka 6-chome, Minato-ku, Tokyo 107, Japan

[21] Appl. No.: 799,377

[22] PCT Filed: Feb. 22, 1985

[86] PCT No.: PCT/JP85/00078
§ 371 Date: Oct. 17, 1985
§ 102(e) Date: Oct. 17, 1985

[87] PCT Pub. No.: WO85/03861
PCT Pub. Date: Sep. 12, 1985

[30] Foreign Application Priority Data

Mar. 1, 1984 [JP] Japan ................... 59-37285

[51] Int. Cl.$^4$ ............... A61K 7/46; C11B 9/00
[52] U.S. Cl. ................................ 252/522 A
[58] Field of Search ............ 252/522 R, 522 A

[56] References Cited

U.S. PATENT DOCUMENTS 4,067,824 1/1979 Teng et al. ............. 252/522 A

FOREIGN PATENT DOCUMENTS

| | | | |
|---|---|---|---|
| 37825 | 11/1973 | Japan | 252/522 A |
| 32134 | 3/1978 | Japan | 252/522 A |
| 160739 | 12/1979 | Japan | 252/522 A |
| 77359 | 5/1984 | Japan | 252/522 A |

Primary Examiner—Werren B. Lone
Attorney, Agent, or Firm—Jordan and Hamburg

[57] ABSTRACT

The present invention relates to a process for the preparation of solid perfumes, which comprises mixing a mixture formed by adding a perfume oil to an alcohol solution containing 1 to 5% of hydroxypropylcellulose with a saturated solution of dibenzylidenesorbitol in N-methyl-2-pyrrolidone to inactivate the perfume oil and the alcohol and form a solid perfume which is hardly volatile and has a persistent fragrance.

1 Claim, No Drawings

PROCESS FOR PREPARATION OF SOLID PERFUMES

TECHNICAL FIELD

The present invention relates to a process for the preparation of solid perfumes which are hardly volatile and have a persistent fragrance.

BACKGROUND ART

A perfume formed by dissolving a perfume oil in an alcohol is widely used, but this perfume is defective in that the fragrance is not persistent. Although a solid perfume is proposed, the exhalation quantity of the fragrance is smaller than that of a liquid perfume since the perfume is solid.

Although Japanese Patent Publication No. 37825/73 proposes a process for preparing a solid perfume, this process is defective in that a synthetic thermoplastic resin should be used as a starting material for forming a solid perfume and the exhalation quantity of the fragrance is small because the formed perfume is completely solid. Disclosure of the Invention It is a primary object of the present invention to develop a process for the preparation of solid perfumes having a persistent fragrance, and this object can be attained by mixing a mixture formed by adding a perfume oil to an alcohol solution containing 1 to 5% of hydroxypropylcellulose with a saturated solution of dibenzylidenesorbitol in N-methyl-2-pyrrolidone to form a gel-like solid mixture in which the alcohol is inactivated and the fragrance is persistent.

BEST MODE FOR CARRYING OUT THE INVENTION

Either a natural perfume oil or a synthetic perfume oil can be used in the present invention, and either an animal oil or a vegetable oil may be used as the natural perfume oil. Either ethyl alcohol or methyl alcohol can be used as the alcohol.

The solid perfume obtained according to the process of the present invention is not completely solidified but is in a gel-like state resembling coagulated gelatin. If the perfume is completely solidified, the persistency of the fragrance is increased but the exhalation quantity of the fragrance is reduced and any satisfactory fragrance can hardly be obtained. For this reason, in the present invention, the perfume is not completely solidified. The gel-like solid perfume prepared according to the present invention has an improved fragrance persistency over that of a liquid perfume and this persistency is comparable to that of a completely solidified perfume, and the exhalation quantity of the fragrance is comparable to that of a liquid perfume.

The reason why a small amount of hydroxypropylcellulose is dissolved in the alcohol in the process of the present invention is that the alcohol is in-activated and the volatility at normal temperature is reduced by incorporation of hydroxypropylcellulose. In the process of the present invention, dibenzylidenesorbitol is added to gelatinize and inactivate the perfume oil to control scattering of the gragrance.

N-Methyl-2-pyrrolidone is a liquid which has a reduced volatility at normal temperature and a high dissolving power to dibenzylidene sorbitol and is odorless and light-colored. Accordingly, N-methyl-2pyrrolidone is suitable for assisting the gelatinizing action of dibenzylidenesorbitol. Moreover, N-methyl-2-pyrrolidone has no substantial environment-contaminating toxicity.

The methods and times for mixing the respective components will now be described.

(1) Mixing of Alcohol, Hydroxypropylcellulose and Perfume Oil

The components are slowly stirred and mixed for 1 to 3 hours by using a stirrer rotated at 50 to 100 rpm.

(2) Mixing of Mixture Formed in (1) Above with Saturated Solution of Dibenzylidenesorbitol in N-Methyl-2-pyrrolidone The saturated solution is slowly dropped to the mixture (1) being stirred at a rate lower than 50 rpm, and the mixture is stirred for 1 to 10 minutes and allowed to stand still, whereby a jelly-like solid perfume is obtained.

Sometimes, a powder of calcium silicate may be added to increase the fragrance persistency according to the intended application.

The present invention will now be described in detail with reference to the following examples.

EXAMPLE 1

Hydroxypropylcellulose was dissolved at a concentration of 3% by weight in ethyl alcohol having a concentration of 95%, and lavender oil was incorporated in an amount of 20% by weight into the solution. The mixture was stirred for 2 hours. Separately, dibenzylidenesorbitol was dissolved in N-methyl-2-pyrrolidone to form a saturated solution. The former mixture was mixed with the latter solution at a weight ratio of 95/5 and the mixture was stirred for 8 minutes, whereby a solid perfume having a fragrance of lavender was prepared.

EXAMPLE 2

A solid perfume having a fragrance of jasmine was prepared in the same manner as described in Example 1 except that jasmine oil was used instead of lavender oil used in Example 1.

EXAMPLE 3

Hydroxypropylcellulose was dissolved at a concentration of 1% by weight in ethyl alcohol having a concentration of 99%, and geraniol was incorporated in an amount of 5% by weight into the solution. The mixture was stirred for 1 hour. Separately, dibenzylidenesorbitol was dissolved in N-methyl-2-pyrrolidone to form a saturated solution. The former mixture was mixed with the latter solution at a mixing weight ratio of 96/4, and the mixture was stirred for 2 minutes to prepare a solid perfume having a fragrance of rose.

EXAMPLE 4

A solid perfume having a fragrance of lemon was prepared in the same manner as described in Example 3 except that citronellal was used instead of geraniol used in Example 3.

Industrial Applicability

As is apparent from the foregoing description, according to the process of the present invention for the preparation of solid perfumes, both the perfume oil and the alcohol are inactivated and they are formed into a gel-like solid perfume. Accordingly, the persistency of the fragrance is increased and the exhalation quantity of the fragrance is large. By dint of these characteristics, the solid perfume prepared according to the process of the present invention can be used in various fields

What is claimed is:

1. A process for the preparation of solid perfumes, which comprises mixing a mixture formed by adding a perfume oil to an alcohol solution containing 1 to 5% of hydroxypropylcellulose with a saturated solution of dibenzylidenesorbitol in N-methyl-2-pyrrolidone to form a gel-like solid.

* * * * *